US010329217B2

(12) United States Patent
Bunquin et al.

(10) Patent No.: US 10,329,217 B2
(45) Date of Patent: Jun. 25, 2019

(54) MULTIMETALLIC CATALYSTS FOR SELECTIVE HYDROGENATION OF DIENES AND ACETYLENES, AND PURIFICATION OF OLEFIN FEEDSTOCKS (71) Applicant: UCHICAGO ARGONNE, LLC, Chicago, IL (US)

(72) Inventors: Jeffrey C. Bunquin, Westmont, IL (US); Magali Ferrandon, Downers Grove, IL (US); Massimiliano Delferro, Chicago, IL (US)

(73) Assignee: UChicago Argonne, LLC, Chicago, IL (US)

( * ) Notice: Subject to any disclaimer, the term of this patent is extended or adjusted under 35 U.S.C. 154(b) by 0 days.

(21) Appl. No.: 15/484,928

(22) Filed: Apr. 11, 2017

(65) Prior Publication Data
US 2018/0290948 A1  Oct. 11, 2018

(51) Int. Cl.
C07C 5/09 (2006.01)
C07C 5/05 (2006.01)
B01J 23/42 (2006.01)

(52) U.S. Cl.
CPC .............. C07C 5/09 (2013.01); B01J 23/42 (2013.01); C07C 5/05 (2013.01); C07C 2521/02 (2013.01); C07C 2521/08 (2013.01); C07C 2523/06 (2013.01); C07C 2523/42 (2013.01); C07C 2523/60 (2013.01)

(58) Field of Classification Search
CPC ............ C07C 2523/42; C07C 2523/44; C07C 2523/46; C07C 7/163; C07C 7/167; C10G 2300/1088; C10G 2300/4018; C10G 2400/20; C10G 45/34; B01J 21/04; B01J 23/50; B01J 23/62; B01J 23/622; B01J 23/626; B01J 23/892; B01J 23/8926; B01J 35/0013; B01J 35/006; B01J 35/008; B01J 37/0211; B01J 37/0213
See application file for complete search history.

(56) References Cited

U.S. PATENT DOCUMENTS 5,362,378 A * 11/1994 Borghard ............. B01J 29/7007
208/135
7,550,637 B2 * 6/2009 Lowe ...................... B01J 23/62
585/259
2006/0004228 A1  1/2006 Hazin

FOREIGN PATENT DOCUMENTS

| KR | 10-2011-078241 A | 7/2011 |
| KR | 10-2012-007764 A | 1/2012 |
| WO | WO-2010/057663 A1 | 5/2010 |
| WO | WO-2013/021020 A1 | 2/2013 |
| WO | WO-2013/021034 A1 | 2/2013 |

OTHER PUBLICATIONS

Aiju, Xu, et al., "Study on Catalytic Performance of Fine Ferrite Derived from Open-Heath Dust," Journal of Functional Materials, vol. 38, No. 6, 2007, pp. 447-452.
Aiju, Xu, et al., "Study on M—Fe—O Catalysts for Oxidative Dehydrogenation of Propane to Propene," Journal of Molecular Catalysis, vol. 21, No. 5, Oct. 2007, pp. 447-453.
Watanabe, R., "Development of the new catalyst for propane selective dehydrogenation utilizing oxidation-reduction of the perovskite oxide catalyst," Petrotech, 2013, pp. 520-523.
Agafonov, Y.A., et al., "Kinetics and mechanism of the oxidative dehydrogenation of isobutane on cobalt, nickel, and manganese molybdates," Kinetics and Catalysis, Mar. 2007, vol. 48, Issue 2, pp. 255-264.
Al-Ju, et al., "Study on M—Fe—O Catalysts for Oxidative Dehydrogenation of Propane to Propene," Journal of Molecular Catalysts (China), vol. 21, No. 5, pp. 447-452) (Oct. 2007).
Al-Ju, et al., "The study on catalytic performance of fine ferrite derived from open-heath dust," Gongneng Cailiao, 38(6), pp. 927-930 (2007).
Al-Zahrani, S.M., et al., "Activities of γ—$Al_2O_3$-Supported Metal Oxide Catalysis in Propane Oxidative Dehydrogenation," Jan. 2003, vol. 85, Issue 1-2, pp. 57-67.
Bachiller-Baeza, B., et al., "Improved performance of carbon nanofiber-supported palladium particles in the selective 1,3-butadiene hydrogenation: Influence of carbon nanostructure, support functionalization treatment and metal precursor," Catalysis Today, vol. 249, Jul. 1, 2015, pp. 63-71.
Baldi, M., et al., "Propane catalytic oxidation and oxy-dehydrogenation over manganese-based metal oxides," Studies in Surface Science and Catalysis, vol. 119, 1998, pp. 635-640.
Baldi, M., et al., "Evaluation of the mechanism of the oxy-dehydrogenation of propane over manganese oxide," Applied Catalysis A: General, vol. 173, Issue 1, Oct. 11, 1998, pp. 61-74.
Berhault, G., et al., "Preparation of nanostructured Pd particles using a seeding synthesis approach—Application to the selective hydrogenation of buta-1,3-diene," Applied Catalysis A: General, vol. 327, Issue 1, Jul. 31, 2007, pp. 32-43.
Cadus, L., et al., "Characterization of Mo—MnO catalyst for propane oxidative dehydrogenation," Applied Catalysis A: General, vol. 233, Issues 1-2, Jul. 10, 2002, pp. 239-253.
Cadus, L., et al., "Highly effective molybdena-manganese catalyst for propane oxidative dehydrogenation," Catalysis Letters, Nov. 2000, vol. 69, Issue 3-4, pp. 199-202.
Deepyaman, S., et al., "Selective hydrogenation of 1,3-butadiene in mixture with isobutene on a Pd/α-alumina catalyst in a semi-batch reactor," Chemical Engineering Science, vol. 62, Issue 17, Sep. 2007, pp. 4544-4557.
El Kolli, N., et al., "Bimetallic Au-Pd catalysts for selective hydrogenation of butadiene: Influence of the preparation method on catalytic properties," Journal of Catalysis, vol. 297, Jan. 2013, pp. 79-92.
Ermini, V., et al., "Propane oxydehydrogenation over alumina-supported vanadia doped with manganese and potassium," Applied Catalysis A: General, vol. 198, Issues 1-2, May 15, 2000, pp. 67-79.

(Continued)

Primary Examiner — Sharon Pregler
(74) Attorney, Agent, or Firm — Foley & Lardner LLP (57) ABSTRACT A catalyst for hydrogenation reaction processes includes an oxide substrate surface, a $MO_x$ promoter, where M is a transition metal or main group elemental oxide, the promoter being deposited on the substrate, and a platinum group catalytic metal.

7 Claims, 4 Drawing Sheets (56) References Cited

OTHER PUBLICATIONS

Gomez, G., et al., "A theoretical view of 1,3-butadiene selective hydrogenation toward cis-2-butene on Pd-Ni layered catalyst," Applied Surface Science, vol. 353, Oct. 30, 2015, pp. 820-828.
Hou, R., et al., "Effect of oxide supports on Pd-Ni bimetallic catalysts for 1,3-butadiene hydrogenation," Applied Catalysis A: General, vol. 490, Jan. 25, 2015, pp. 17-23.
Hou, R., et al., "Selective hydrogenation of 1,3-butadiene on Pd-Ni bimetallic catalyst: from model surfaces to supported catalysts," J. Catal. 316, 2014, pp. 1-10.
Insorn, P., et al., Selective hydrogenation of mixed C4 containing high vinyl acetylene by Mn—Pd, Ni—Pd and Ag—Pd on Al2O3 catalysts, Catalysis Today, vol. 256, Part 2, Nov. 1, 2015, pp. 223-230.
Jibril, B.Y., "Effects of Food Compositions on Oxidative Dehydrogenation of Propane over Mn—P—O Catalyst," Industrial & Engineering Chemistry Research, 2005, 44(4), pp. 702-706.
Jibril, B.Y., et al., "Propane Oxidative Dehydrogenation over Metal Pyrophosphates Catalysts," Catalysis Letters, Jul. 2001, vol. 74, Issue 3-4, pp. 145-148.
Jugnet, Y., et al., "Selective hydrogenation of 1,3-butadiene on $Pt_3Sn(111)$ alloys: comparison to Pt(111)", Journal of Catalysis, vol. 229, Issue 1, Jan. 1, 2005, pp. 252-258.
Kondratenko, E.V., et al., "Characterisation of vanadium-oxide-based catalysis for the oxidative dehydrogenation of propane to propene," Jun. 2001, vol. 15, Issue 2-4, pp. 175-180.
Lee, D.C., et al., "Selective hydrogenation of 1,3-butadiene on $TiO_2$-modified $Pd/SiO_2$ catalysts," Applied Catalysis A: General, vol. 244, Issue 1, May 8, 2003, pp. 83-91.
Li, X., et al., "Selective Alkane Oxidation by Manganese Oxide: Site Isolation of $MNO_x$ Chains at the Surface of $MnWO_4$ Nanorods", Angew Chem. Int. Ed. Engl, Mar. 14, 2016; 55(12), pp. 4092-4096.
Liu, C., et al., "Hydrogenation of 1,3-butadiene over Au and $Pt/SiO_2$-N catalysts at low temperature," Catalysis Communications, vol. 67, Jul. 5, 2015, pp. 72-77.
Liu, Z., et al., "Single Gold Atoms in Heterogeneous Catalysis: Selective 1,3-Butadiene Hydrogenation over $Au/ZrO_2$," Angew. Chem. Int. Ed. 2006, 45, pp. 6865-6868.
Loffreda, D., et al., "Tuning catalytic reactivity on metal surfaces: Insights from DFT," Journal of Catalysis, vol. 308, Dec. 2013, pp. 374-385.
Lozano, L., et al., "Influence of toluene on the catalytic activity of NiPdCe catalyst for selective hydrogenation of 1,3-butadiene," Fuel, vol. 110, Aug. 2013, pp. 76-82.
Lucci, F.R., et al., "Selective hydrogenation of 1,3-butadiene on platinum-copper alloys at the single-atom limit," Nature Communications, 6, 8550 (2015).
Massard, R., et al., "Strained Pd overlayers on Ni nanoparticles supported on alumina and catalytic activity for buta-1,3-diene selective hydrogenation," Journal of Catalysis, vol. 245, Issue 1, Jan. 1, 2007, pp. 133-143.
Nowinska, K., et al., "Propane oxydehydrogenation over transition metal modified zeolite ZSM-5," Applied Catalysis A: General, vol. 243, Issue 2, Apr. 10, 2003, pp. 225-236.
Palacio, L.A., et al., "Catalytic performance and stability of isomorphic molybdates used for the oxidative dehydrogenation of propane," Reaction Kinetics and Catalysis Letters, May 2005, vol. 85, Issue 1, pp. 175-182.
Palacio, L.A., et al., "Cu, Mn and Co molybdates derived from novel precursors catalyze the oxidative dehydrogenation of propane," Catalysis Today, vol. 107-108, Oct. 30, 2005, pp. 338-345.
Pattamakomsan, K., et al., "Effect of mixed $Al2_2O_3$ structure between ϴ- and $α-Al_2O_3$ on the properties of $Pd/Al_2O_3$ in the selective hydrogenation of 1,3-butadiene," Catalysis Communications, vol. 11, Issue 5, Jan. 25, 2010, pp. 311-316.
Pattamakomsan, K., et al., "Selective hydrogenation of 1,3-butadiene over Pd and Pd-Sn catalysts supported on different phases of alumina," Catalysis Today, vol. 164, Issue 1, Apr. 30, 2011, pp. 28-33.
Piccolo, L., et al., "Pd-Au single-crystal surfaces: Segregation properties and catalytic activity in the selective hydrogenation of 1,3-butadiene," Surface Science, vol. 592, Issues 1-3, Nov. 1, 2005, pp. 169-181.
Piccolo, L., et al., "Tuning the shape of nanoparticles to control their catalytic properties: selective hydrogenation of 1,3-butadiene on $Pd/Al_2O_3$," Phys. Chem. Chem. Phys. 2008, 10, pp. 5504-5506.
Qingjie, G., et al., "Oxidative dehydrogenation of ethane and propane over Mn-based catalysts," Catalysis Letters, Aug. 2000, vol. 68, Issue 1-2, pp. 59-62.
Sadykov, et al., "Oxidative dehydrogenation of propane over monoliths at short contact times," Catalysis Today, vol. 61, Issues 1-4, pp. 93-99 (Aug. 2000).
Silvestre-Albero, J., et al., "Atmospheric pressure studies of selective 1,3-butadiene hydrogenation on well-defined $Pd/Al_2O_3/$ NiAl(110) model catalysts: Effect of PD particle size," Journal of Catalysis, vol. 240, Issue 1, May 15, 2006, pp. 58-65.
Stern, D.L., et al., "Propane Oxydehydrogenation over Molybdate-based Catalysts," Journal of Catalysis, vol. 167, Issue 2, Apr. 15, 1997, pp. 550-559.
Verdier, S., et al., "$Pd-Sn/Al_2O_3$ catalysts from colloidal oxide synthesis: II. Surface characterization and catalytic properties for buta-1,3-diene selective hydrogenation," Journal of Catalysis, vol. 218, Issue 2, Sep. 10, 2003, pp. 288-295.
Yan, H., et al., "Single-Atom $Pd_1$/Graphene Catalyst Achieved by Atomic Layer Deposition: Remarkable Performance in Selective Hydrogenation of 1,3-Butadiene," J. Am. Chem. Soc., 2015, 137(33), pp. 10484-10487.
Yi, H., et al., "Precisely Controlled Porous Alumina Overcoating on Pd Catalyst by Atomic Layer Deposition: Enhanced Selectivity and Durability in Hydrogenation of 1,3-Butadiene," ACS Catal., 2015, vol. 5(5), pp. 2735-2739.
Zhang, X., et al., "Catalysis by Gold: Isolated Surface $Au^{3+}$ Ions are Active Sites for Selective Hydrogenation of 1,3-Butadiene over $Au/ZrO_2$ Catalysts," Angew. Chem. Int. Ed., vol. 44, Issue 43, Nov. 4, 2005, pp. 7132-7135.
Zhang, X., et al., "Comparative study of $Au/ZrO_2$ catalysts in CO oxidation and 1,3-butadiene hydrogenation," Catalysis Today, vol. 122, Issues 3-4, Apr. 30, 2007, pp. 330-337.
Zhang, Z.C., et al., "Pd Cluster Nanowires as Highly Efficient Catalysts for Selective Hydrogenation Reactions," Chem. Eur. J. Feb. 27, 2012, vol. 18, Issue 9, pp. 2639-2645.
Zhu, H., et al., "Study of Mn-based Catalysts for Oxidative Dehydrogenation of Cyclohexane to Cyclohexene," Catalysis Letters, Nov. 2005, vol. 105, Issue 1-2, pp. 29-33.

* cited by examiner

MULTIMETALLIC CATALYSTS FOR SELECTIVE HYDROGENATION OF DIENES AND ACETYLENES, AND PURIFICATION OF OLEFIN FEEDSTOCKS

STATEMENT OF GOVERNMENT INTEREST

The United States Government claims certain rights in this invention pursuant to Contract No. DE-AC02-06CH11357 between the U.S. Department of Energy and UChicago Argonne, LLC, as operator of Argonne National Laboratory.

FIELD OF THE INVENTION

The present invention generally relates to catalysts, specifically to multimetallic catalysts.

BACKGROUND

This section is intended to provide a background or context to the invention recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

Alkenes are important hydrocarbon intermediates used in the production of various polymers and liquid fuels (i.e. isobutene dimerization to isooctane). Dienes (e.g., 1,3-butadiene) and acetylenes (e.g., alkynes, vinylacetylene) are common unsaturated olefin feedstock contaminants that decompose and deactivate catalysts used in polymerization and olefin dimerization/oligomerization processes. Thus, selective removal via catalytic hydrogenation of these unsaturated dienes and acetylene contaminants is a critical processing/purification step in the industrial refining of mono-olefin feedstocks (e.g., ethylene, propylene and butenes). More specifically, highly selective hydrogenation of dienes and acetylenes (e.g., 1,3-butadiene and vinylacetylenes to butenes) with minimal hydrogenation of mono-olefins to the lower value alkane products is warranted since chemoselective catalysts that completely discriminate the contaminants from the hydrogenation-sensitive mono-olefin are extremely rare. For example, a catalyst that can semi-hydrogenate 1,3-butadiene and vinylacetylene contaminants to mono-olefins (1-butene) in a feedstock comprised mainly of the mono-olefin (1-butene) is one way to decrease the concentration of the unwanted contaminants, and increase the amount of desirable mono-olefin component. As a result, the overall efficiency of olefin polymerization and dimerization/oligomerization processes would also improve.

Conventional diene and acetylenes hydrogenation techniques employ multimetallic nanoparticles (i.e. palladium (Pd), platinum (Pt), and silver (Ag)) that are often promoted by other transition metals, such as nickel, which is toxic. Because these techniques use bulk catalytic structures (i.e. nanoparticles), the overall atom efficiency of the hydrogenation catalysts is low. Other strategies may involve poisoning nanoparticle or bulk active surfaces with organosulfur ligands that are labile, impacting long-term catalyst stability. Moreover, most hydrogenation catalysts for dienes and acetylenes are used at low temperatures (e.g., 50° C.) due to their susceptibility to coke deposition, which blocks catalytic sites and ultimately results in catalyst deactivation. Since most of these catalysts are mainly evaluated at lower temperatures, low diene and acetylene conversions are generally observed.

A need exists for improved technology, including a selective catalyst for hydrogenation of dienes (e.g., 1,3-butadiene) and acetylenes, and a method for hydrogenation of these compounds.

SUMMARY

One embodiment of the invention relates to a catalyst for hydrogenation reaction processes, the catalyst including a substrate surface consisting essentially of an oxide substrate, a promoter consisting essentially of $MO_x$ where M is a transition metal or main group elemental oxide, the promoter deposited on the substrate, and a catalytic metal consisting essentially of a platinum group element.

In one embodiment, the promoter further comprises an alkali element, an alkaline earth element, a metalloid, or a post-transition metal. In one embodiment, the promoter comprises either boron (B) or tin (Sn). In one embodiment, the catalyst comprises the promoter in an amount ranging from about 1 wt % to about 10 wt %. In one embodiment, the catalyst comprises less than 1 wt. % catalytic metal.

Another embodiment of the invention relates to a method of forming a mixture of 1-butene and 2-butenes. The method includes exposing a C4 feedstock contaminant to a catalyst comprising $M'/M/E_xO_y$ where the catalyst M' is a Pt group metal, M is a transition metal or a main group element material and E is Si, Al, Ti, or Zr and x and y represent stoichiometric amounts and forming the mixture of 1-butene and 2-butenes.

In one embodiment, the step of forming the mixture comprises a selectivity for 1-butene and 2-butene of at least 80%. In one embodiment, the step of exposing the C4 feedstock contaminant is at a temperature of approximately 200° C. In one embodiment, at least 70% of the C4 feedstock contaminant is converted to the mixture. In one embodiment, the C4 feedstock contaminant is 1,3-butadiene, vinylacetylene, or a combination thereof.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The disclosure will become more fully understood from the following detailed description, taken in conjunction with the accompanying figures, in which.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

In the present disclosure, multimetallic platinum-based catalysts are fabricated for the selective hydrogenation of 1,3-butadiene to mixtures of butenes where 1-butene is a main product and minimal formation of the exhaustively hydrogenated product, n-butane, is observed. Catalysts used in the synthesis procedure have improved stability, high selectivity to monoolefins, and increased atomic efficiency of the catalytic metal.

A general synthetic approach to hydrogenation of 1,3-butadiene to mixtures of butenes using the catalysts of the present disclosure is shown below. In the below reaction scheme, catalyst M'/M/$E_xO_y$ comprises a catalytically active platinum (Pt) group metal (M'), at least one promoter (M) comprising a transition metal or main group element, and a substrate surface ($E_xO_y$).

Reaction Scheme I

The substrate surface comprises a support material with the general formula of $E_xO_y$, as stated above. In some embodiments, the support material is selected from an oxide substrate such as zirconia ($ZrO_2$), titania ($TiO_2$), silica ($SiO_2$) or alumina ($Al_2O_3$), or the like. Further, the substrate may comprise a substrate surface composed of any of the preceding. Prior attempts at using silica with platinum catalysts have suffered from short catalyst lifespans due to fouling of the catalyst active sites, and as a result, poor performance. In one embodiment, the silica substrate is a high-surface-area substrate and may be formed as a membrane, as a particle (e.g. a bead or powder), or as some other structure. The substrate surface may be a porous body. In various embodiments the substrate surface has a surface area, incrementally, of at least 1 $m^2/g$, at least 5 $m^2/g$, at least 10 $m^2/g$, at least 20 $m^2/g$, at least 40 $m^2/g$, at least 60 $m^2/g$, at least 80 $m^2/g$, and/or at least 100 $m^2/g$. In some embodiments, the substrate surface has a surface area, incrementally, of up to about 10000 $m^2/g$, up to 5000 $m^2/g$, up to 1000 $m^2/g$, up to 500 $m^2/g$, up to 250 $m^2/g$, up to 150 $m^2/g$, up to 120 $m^2/g$, up to 100 $m^2/g$, up to 80 $m^2/g$, and/or up to 60 $m^2/g$. In other embodiments, substrate surface may have a surface area of more than 10,000 $m^2/g$ or less than 1 $m^2/g$. The supports may be microporous, mesoporous, non-porous or macroporous in various embodiments. The particles of alumina/silica may be, in one embodiment, of any size appropriate for the scale of the structure.

In some embodiments, the promoter comprises a transition metal or main group element (M). In some embodiments, the promoter comprises an oxide layer of the transition metal or main group element. Metal oxide promoters improve catalyst stability by slowing catalyst deactivation. In particular embodiments, metal oxide promoters have the general formula $MO_x$, where M is a transition metal or main group metal. Specifically, $MO_x$ may include, but is not limited to, $TiO_2$, $ZrO_2$, $CoO_x$ (where x ranges between 1 and 1.5), ZnO, $MnO_x$ (where x ranges between 1 and 4), $B_2O_3$, $Al_2O_3$, and $Ga_2O_3$. The transition metal may be, in certain embodiments, a first row transition metal. The promoter has a thickness. In one embodiment, the promoter does not provide complete coverage of the substrate surface. For example, the promoter may be deposited by a thin film deposition technique to form a partial monolayer atop the substrate surface. In another embodiment, a complete monolayer of the promoter is formed. In yet another embodiment, the promoter may include at least 2 layers, at least 3 layers, at least 4 layers, at least 5 layers, and/or at least 10 layers. In one embodiment, the promoter comprises multiple metal oxides. In other embodiments, the promoter consists essentially of a single metal oxide, preferably boron oxide.

The catalytic metal (M') includes a catalytically active material including, but are not limited to, platinum and platinum group metals. In one embodiment, the catalytic metal consists essentially of platinum. In another embodiment, the catalytic metal consists of platinum-containing material. The types of Pt and distribution of Pt sites (isolated vs clusters vs particles) vary depending on the synthesis method. Depositing using ALD, solution-phase organometallic synthesis or like processes (as opposed to solution-phase impregnation methods) leads to increased amounts of monodispersed and isolated catalytic metal sites. Superior hydrogenation activity and selectivity may be achieved using monodispersed Pt sites or small clusters as opposed to nanoparticles. In one embodiment, catalytic metal loading on the catalyst comprises less than 1 wt. % catalytic metal. In another embodiment, catalytic metal loading on the catalyst comprises less than 0.5 wt. % catalytic metal. In yet another embodiment, catalytic metal loading on the catalyst comprises less than 0.1 wt. % catalytic metal (i.e. about 0.08 wt. %). In one embodiment, low catalytic metal loading is desired in the range of about 0.1 wt % to about 2 wt %. In another embodiment, the catalytic metal is loaded in the range of about 0.1 wt % to about 1 wt %. Catalytic metal loading at higher concentrations (i.e. about 5 wt % to about 10 wt %) would form undesired nanoparticles.

Various synthesis methods may be used for depositing the catalytic metal, the transition metal and the silica. For example, synthesis methods may include thin-film deposition techniques, such as Atomic Layer Deposition (ALD), solution processes (Sol'n) or strong electrostatic adsorption (SEA). In some embodiments, one or more of the catalytic metal, the promoter and the substrate surface can be form by ALD. ALD utilizes alternating exposures between precursors (i.e. in a gaseous form) and a solid surface to deposit materials in a monolayer-by-monolayer fashion. This process can provide uniformity of the coatings in many embodiments, including on nanoporous substrate materials. A catalyst system may be manufactured using a combination of deposition methods. Further, the number of cycles for each deposition may be varied, for example, the number of ALD cycles. In some embodiments, this process also allows good control over the thickness and composition of the coatings. In one embodiment, ALD was used to deposit both Pt and ZnO. In another embodiment, ALD was used to deposit ZnO and a solution-phase process was used to deposit platinum. In yet another embodiment, SEA was used to deposit ZnO and a solution-phase process was used to deposit platinum.

The types of Pt and distribution of Pt sites (isolated vs clusters vs particles) vary depending on the synthesis method. For some embodiments, it is advantageous to use ALD to deposit metals as compared to solution-phase synthesis methods. For example, in certain embodiments, catalysts where the Pt had been deposited by ALD exhibited higher activity and stability because the Pt showed a greater polydispersity character. Synthesis methods that effect high platinum site dispersity (i.e., more isolated sites or small clusters) are optimum for the catalyst fabrication. Traditional Pt impregnation methods that form Pt|Zn nanoparticles are not selective for hydrogenation; mono-olefins (e.g., 1-butene and propene) and dienes (e.g., 1,3-butadiene) are both hydrogenated even at room temperature. Platinum to promoter ratio has a larger impact on catalytic activity than the deposition methods used. Improved Pt dispersion can be achieved at a higher loading of the promoter; substrates with a monolayer/saturated with promoters are more stable compared to substrates with lower promoter coverages (50% of a monolayer or less).

The catalytic metal may include a plurality of promoters. In some embodiments, a promoter is applied on top of the active catalyst: M/M'/E$_x$O$_y$ (i.e. Zn/Pt/SiO$_2$, where Zn functions as the promoter). In yet other embodiments, two or more different promoters may sandwich the active catalyst: M/M'/E$_x$O$_y$ (i.e. Zn/Pt/B/SiO$_2$; where the deposition may be sequenced as (1) B, (2) Pt and (3) Zn); the boron promoter is an under layer while ZnO is an overcoat. In another embodiment, the deposition may be sequenced as (1) Zn, (2) Pt, and (3) B since both Zn and B may be considered promoters. Promoters may include various cations such as $Zn^{2+}$, $B^{3+}$, or other cations selected from the group consisting of an alkali element, an alkaline earth element, a metalloid, and a post-transition metal. Thus, in the final composition the promoter layer may be an oxide of such materials, for example $B_2O_3$ or ZnO. Unless otherwise indicated, the descriptions of the catalyst materials herein shall use a short-hand nomenclature referring to the deposited element rather than the cation form.

As the subsequent explanations will detail, Tables 1 and 2 show empirical results where the feedstock comprises only one C4 feedstock contaminant species: 1,3-butadiene. These results show that with the exception of Pt/Zn/SiO$_2$, the other catalysts (i.e. Pt/B/SiO$_2$, B/Pt/Zn/SiO$_2$, and Zn/Pt/B/SiO$_2$) all exhibit selectivity to semihydrogenation (i.e. hydrogenation of only one C=C bond) to give mixtures of products composed mainly of monoalkenes (i.e. 1-butene and 2-butenes) and low levels of n-butane (i.e. less than 10%) at 200° C.

TABLE 1

Hydrogenation of 1,3-butadiene at 100° C.

| Catalyst | 1,3-butadiene conversion (%) | Selectivity (%) | | | |
|---|---|---|---|---|---|
| | | 1-butene | cis-2-butene | trans-2-butene | n-butane |
| Pt/B/SiO$_2$ | 26.5 | 55.4 | 11.6 | 17.1 | 16.0 |
| Pt/Zn/SiO$_2$ | 47.5 | 48.0 | 9.5 | 14.2 | 28.3 |
| B/Pt/Zn/SiO$_2$ | 3.3 | 37.2 | 19.9 | 18.5 | 24.1 |
| Zn/Pt/B/SiO$_2$ | 18.1 | 56.0 | 11.4 | 14.5 | 18.1 |

TABLE 2

Hydrogenation of 1,3-butadiene at 200° C.

| Catalyst | 1,3-butadiene conversion (%) | Selectivity (%) | | | |
|---|---|---|---|---|---|
| | | 1-butene | cis-2-butene | trans-2-butene | n-butane |
| Pt/B/SiO$_2$ | 91.4 | 47.1 | 19.4 | 30.4 | 3.1 |
| Pt/Zn/SiO$_2$ | 100.0 | 8.3 | 16.5 | 28.6 | 47.6 |
| B/Pt/Zn/SiO$_2$ | 31.1 | 45.9 | 20.6 | 27.8 | 5.7 |
| Zn/Pt/B/SiO$_2$ | 81.6 | 51.8 | 17.8 | 27.9 | 2.5 |

Tables 1 and 2 illustrate the effect of promoters on the selectivity and activity of multimetallic catalysts in the selective hydrogenation of 1,3-butadiene. In comparing the selectivity and activity of Pt/B/SiO$_2$ catalyst with the selectivity and activity of Pt/Zn/SiO$_2$ catalyst at 200° C. (Table 2), while both catalysts share similar conversion percentages of 1,3-butadiene at over 90%, the Zn promoter yields a much lower selectivity to butenes than the B promoter (approximately 52.5% versus a 96.9% selectivity, respectively). Similar trends are observed at 100° C. (i.e. the Zn promoter gives a lower selectivity (71.7%) to butenes than the B promoter (84%)), though conversion of 1,3-butadiene does not exceed 50% for either Pt/B/SiO$_2$ (26.5%) or Pt/Zn/SiO$_2$ (47.5%). In one embodiment, catalysts with boron promoters more effectively suppress coking relative to catalysts without boron promoters. In other embodiments, catalyst selectivity may be a result of different factors such as electronic effects of the promoter. Overall, the boron promoter was far superior in minimizing n-butane formation for both temperatures, and the higher temperature also yielded high conversions of 1,3-butadiene for all catalysts. The zinc promoter yielded greater quantities of n-butane across both temperatures, ranging from about 28% at 100° C. to close to 50% at 200° C.

Tables 1 and 2 also illustrate the effect of temperature on the selectivity and activity of B/Pt/Zn/SiO$_2$ and Zn/Pt/B/SiO$_2$ catalysts, respectively, in the selective hydrogenation of 1,3-butadiene. At 100° C., conversion of 1,3-butadiene is typically under 20% for both the B/Pt/Zn/SiO$_2$ catalyst (3.3%) and the Zn/Pt/B/SiO$_2$ catalyst (18.1%). At 200° C., conversion of 1,3-butadiene is much higher when comparing with 100° C.—B/Pt/Zn/SiO$_2$ catalyst (31.1%) and the Zn/Pt/B/SiO$_2$ catalyst (81.6%). Lower temperatures also yield higher quantities of n-butane than when compared at the higher temperature (B/Pt/Zn/SiO$_2$ catalyst: 24.1% at 100° C. versus 5.7% at 200° C.; Zn/Pt/B/SiO$_2$ catalyst: 18.1% at 100° C. versus 2.5% at 200° C.). The decrease in unwanted n-butane side product at elevated temperatures may be caused by catalyst thermal activation at the higher temperatures. At 200° C., high conversion and high selectivity was observed. For example, for B/Pt/Zn/SiO$_2$ catalyst, the reaction proceeds with a 94.3% selectivity of either 1-butene or 2-butenes at 200° C. whereas at 100° C., the reaction proceeds with a 75.9% selectivity of either 1-butene or 2-butenes. For the Zn/Pt/B/SiO$_2$ catalyst, the reaction proceeds with a 97.5% selectivity of either 1-butene or 2-butenes at 200° C. whereas at 100° C., the reaction proceeds with a 81.9% selectivity of either 1-butene or 2-butenes. Thus, at elevated temperatures, 1,3-butadiene hydrogenation reactions using the multimetallic catalysts disclosed above proceed with higher selectivity for butenes and higher activity of the catalyst.

In some embodiments, the catalyst disclosed herein may be formed as a promoter deposited on the substrate and a catalytic metal deposited on the promoter. In another embodiment, the promoter and the catalytic metal may be interchanged by being introduced to the substrate surface simultaneously. In some embodiments, the catalytic metal and the promoter may be discrete layers. In some embodiments, the catalytic metal and/or the promoter are each a monolayer or sub-monolayer. In some embodiments, the catalytic metal and/or the promoter each may include multiple layers. In some embodiments, the catalytic metal and/or the promoter each may include at least 2 layers, at least 3 layers, at least 4 layers, at least 5 layers, and/or at least 10 layers. In other embodiments, the catalytic metal and/or the promoter are each formed of isolated sites or extended structures such as clusters, islands, particles, or flakes. In a preferred embodiment, the catalytic metal and/or the promoter are each formed of isolated sites or small clusters. The catalyst may, in some embodiments, be incorporated with alkali elements (i.e. Li, Na, K), alkaline earth elements (i.e. Mg, Ca), metalloids (i.e. B), or post-transition metals (i.e. Sn). In a particular embodiment, catalysts with boron promoter are observed to suppress coking and deactivation relative to catalysts without boron promoters.

The catalyst may facilitate high selectivity and conversion rate for diene hydrogenation to mono-olefin products, with minimum formation of exhaustively hydrogenated product (alkane), when compared to known materials utilizing the catalytic metal on a silica substrate surface or the catalytic metal with other substrate surfaces such as alumina. In one embodiment, the catalyst is made by thin film deposition techniques, including solution-phase synthesis (i.e. strong electrostatic adsorption and surface organometallics) and gas-phase synthesis (i.e. atomic layer deposition), by depositing the promoter on the substrate surface.

In one example, a synthetic approach in forming the catalyst of the present disclosure is shown below. In the below reaction scheme, M' is a catalytically active platinum (Pt) group metal, M is a promoter comprising a transition metal or main group element, and E is a substrate surface Si, Al, Ti, Zr, or the like.

Reaction Scheme II

In the catalyst formation steps of Reaction Scheme II, the promoter ion may be deposited via (a) gas-phase deposition (ALD) at about 75° C. to about 200° C., (b) solution-phase organometallic grafting at room temperature, or (c) strong electrostatic adsorption. The catalytic metal (Pt) may be deposited via (a) gas-phase deposition (ALD) at about 90° C. to about 200° C. or (b) solution-phase organometallic grafting at room temperature. In other embodiments, Reaction Scheme II may be modified such that the catalytically active platinum (Pt) group metal (M') is installed prior to depositing the promoter (M).

For the hydrogenation of 1,3-butadiene to mixtures of butenes shown above in Reaction Scheme I, in embodiments where the concentration of exposed catalyst (Pt) sites are low, the catalytic metal surface is exposed, meaning there is no overcoat deposited on the catalytic metal. However, overcoats have been observed to increase stability against active site sintering. In one embodiment, an overcoat, such as alumina, can be utilized as both a promoter and to stabilize active catalytic sites, thereby improving stability of the catalyst.

Reaction Scheme I may be performed at a range of temperatures. The catalyst disclosed herein may feature the use of promoters, which significantly suppress coke deposition under harsh reaction conditions (i.e. 200° C. or higher). Moreover, metal oxide promoters improve catalyst stability and in certain embodiments presented herein, are recyclable after multiple-cycle hydrogenations at 200° C. In one embodiment, the range of temperatures for catalyzing a 1,3-butadiene hydrogenation reaction is 50° C. to 400° C., 100° C. to 350° C., 150° C. to 300° C., 175° C. to 250° C., and 185° C. to 225° C. At temperatures above approximately 400° C., undesired dehydrogenation reactions become competitive.

Catalysis described herein exhibit a selectivity of at least 80%, at least 90%, at least 92%, at least 94%, at least 95%, at least 96%, at least 98%, at least 99%, or at least 99.5%. In one embodiment, the catalyst is highly selective to butenes (i.e. 1-butene, c-2-butene, and t-2-butene). In one embodiment, the catalyst is applicable for 1,3-butadiene hydrogenation. In one embodiment, the catalyst is applicable for vinylacetylene hydrogenation. In one embodiment, the catalyst is applicable for hydrogenation of the combination of 1,3-butadiene and vinylacetylene in the presence of a high concentration of α-olefin (e.g., 1-butene). In one embodiment, a selectivity of at least 10%, 20%, 30%, 40%, 50%, 60%, 70% or a range of 10-70% to butenes is observed with a Pt/MO$_x$/SiO$_2$ catalyst. In one embodiment, selectivity to butenes is 97% using Pt|B|SiO$_2$ catalysts. Catalysis exhibit a conversion of at least 50%, at least 55%, at least 60%, at least 65%, at least 70%, or at least 75%. In one embodiment, the selectivity is observed after at least 10, at least 20, at least 30, at least 40, at least 50, at least 60, at least 70 hours, or at least 90 hours without catalyst regeneration.

Comparative Example

As the subsequent explanations will detail, FIGS. 1A to 2B show results of gas purification experiments wherein a C4 feedstock comprising mono-olefin 1-butene (95%; Pt|B-|SiO$_2$ catalyst does not react with mono-olefins) with low levels of C4 contaminants (2.5% 1,3-butadiene; 2.5% vinylacetylene) was hydrogenated. Results of the data from FIGS. 1A to 2B include conversion of both C4 contaminants (i.e. 1,3-butadiene and vinylacetylene) without a detectable decline in the main mono-olefin component (i.e. 1-butene) concentration. Thus, the catalysts may be used for purification of mono-olefin feedstocks by selective hydrogenation of 1,3-butadiene and vinylacetylene contaminants in the presence of high concentrations of a mono-olefin (i.e. 1-butene).

Figure 1A:
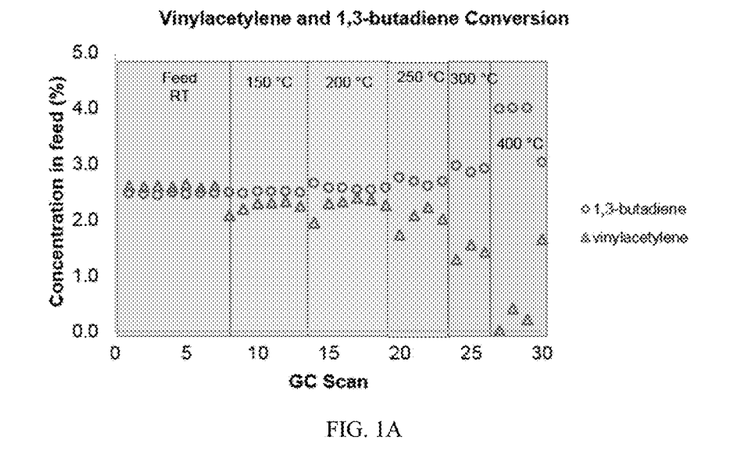
FIGS. 1A to 1D depict the chemoselective hydrogenation of 1,3-butadiene and vinylacetylene in the presence of a large excess of an α-olefin according to one embodiment.

As previously disclosed, 1,3-butadiene and vinylacetylene are common unsaturated C4 feedstock contaminants that decompose and deactivate catalysts (sometimes irreversibly) used in polymerization and dimerization of olefins (e.g., 1-butene, propylene, ethylene). As presented in the general synthetic approach below, Pt/B/SiO$_2$ catalyst is able to preferentially hydrogenate these conjugated C4 olefins/alkynes contaminants in the presence of a large excess of an α-olefin (in this case, 1-butene), with minimal conversion of the α-olefin (i.e. 1-butene).

tration is also observed. As seen previously, when vinylacetylene is absent (as shown in FIG. 1A), conversion of 1,3-butadiene to 1-butene using a Pt/B/SiO$_2$ catalyst exceeds 90%. The concentration of 1-butene minimally changes during hydrogenation with the Pt/B/SiO$_2$ catalyst up to temperatures of 300° C. (FIG. 1B), showing that the catalyst can purify α-olefin feedstocks contaminated by dienes and alkynes.

Figure 1B:
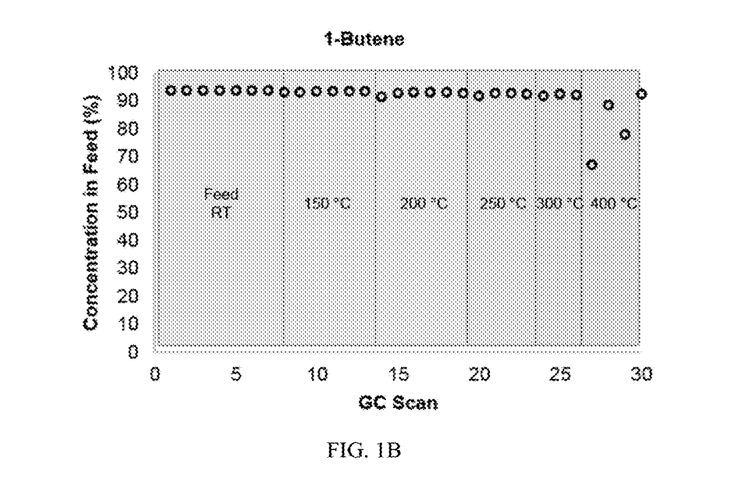
Figure 1C:
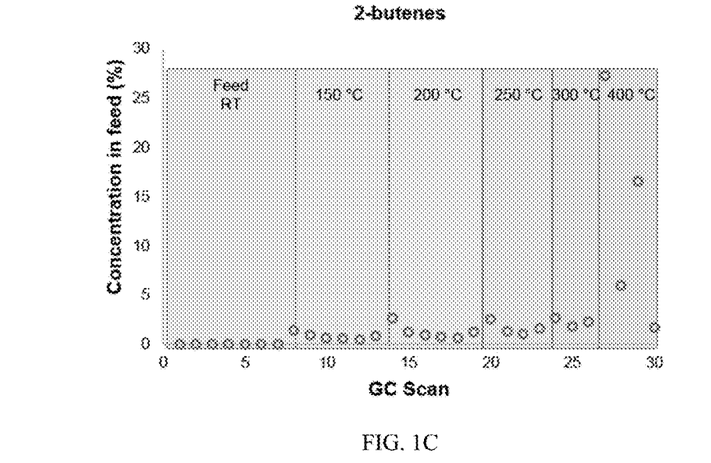
Figure 1D:
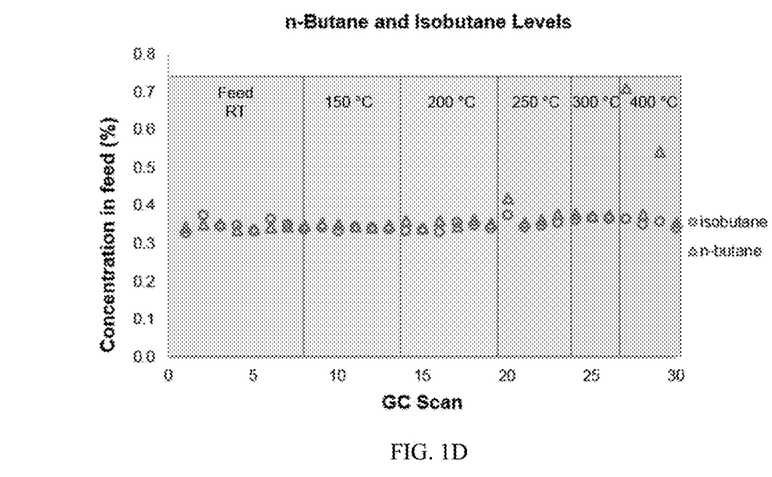

Beyond 300° C. and up to 400° C., concentrations of 1-butene vary from the starting 95% to as low as approximately 60-65%. These variations are likely due to isomerization of 1-butene to 2-butene, which experiences an increase in concentration at the same 300° C. to 400° C. temperature range (FIG. 1C). The catalyst does not convert 1-butene to butane. Even at the elevated temperatures above 300° C., the combined concentrations of 1-butene and 2-butene are at least 95%. As is preferred in diene hydrogenation reactions, side-product formation of butanes, specifically n-butane, is contained at below 1% concentration at all temperatures (FIG. 1D). Thus, the formation of exhaustively hydrogenated C4 hydrocarbons (i.e. butane), is suppressed at temperatures lower than 400° C., confirming that the Pt/B/SiO$_2$ catalyst is non-reactive to α-olefins (i.e. 1-butene).

Figure 2A:
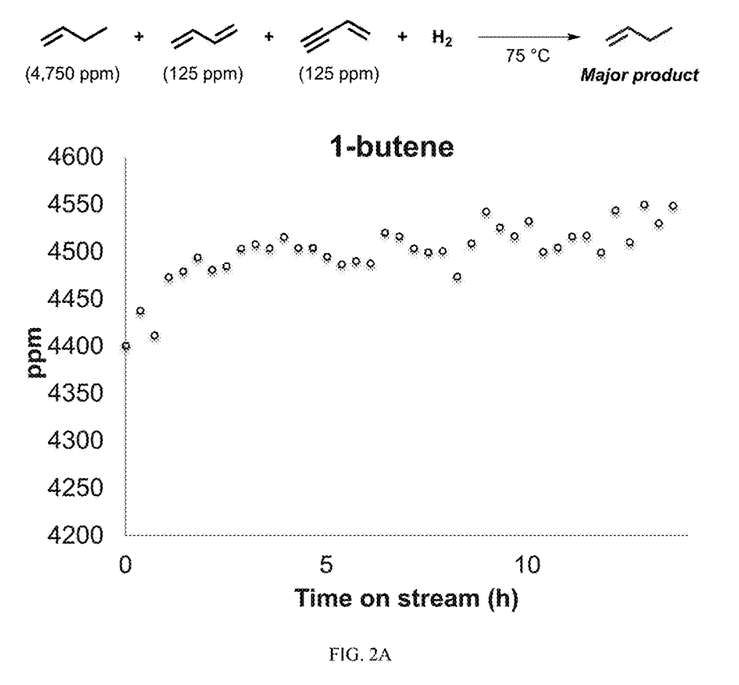
FIGS. 2A and 2B illustrate selective hydrogenation of 1,3-butadiene and vinylacetylene in the presence of a large excess of 1-butene at 75° C. The Pt|B|SiO$_2$ catalyst was pre-activated with H$_2$ at 200° C.
Figure 2B:
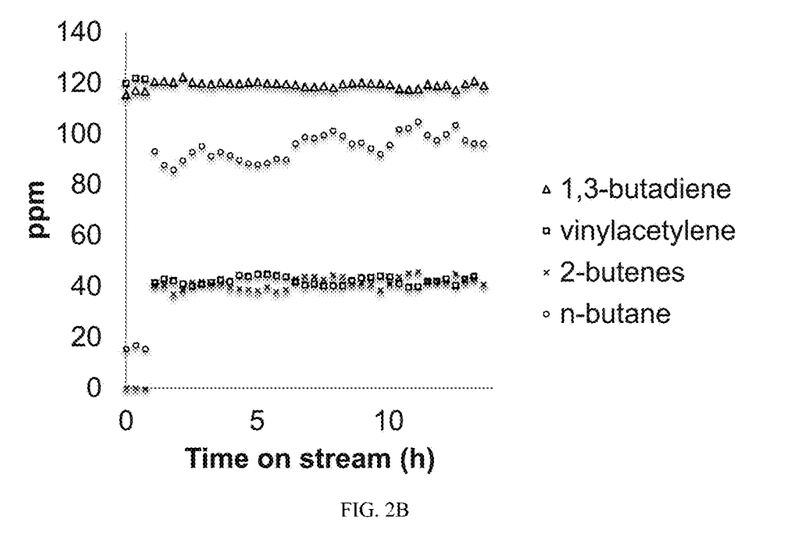

FIGS. 2A and 2B illustrate selective hydrogenation of 1,3-butadiene and vinylacetylene in the presence of a large excess of 1-butene at 75° C. The Pt|B|SiO$_2$ catalyst was Reaction Scheme III The starting feed composition was structured to mimic industrial compositions of α-olefin feeds and contained 95% 1-butene, with low levels of the C4 contaminants 1,3-butadiene (2.5%), and vinylacetylene (2.5%). FIGS. 1A to 1D shows the progression of Reaction Scheme III as temperature is elevated up to approximately 400° C. to understand the thermal activation of the catalyst for chemoselective hydrogenation of the C4 contaminants. At lower temperatures (less than 200° C.), there is little-to-no conversion of vinylacetylene and 1,3-butadiene since the overall concentrations of vinylacetylene and 1,3-butadiene (as well as 1-butene) in the feed are roughly equivalent to the starting feed composition (FIGS. 1A and 1B). As temperature increases past 200° C. to about 300° C., an increase is seen in the concentration of 1,3-butadiene (FIG. 1A); this is due to the semi-hydrogenation of vinylacetylene to 1,3-butadiene and corresponding decreases in vinylacetylene concenpre-activated with H$_2$ at 200° C. Specifically for FIG. 2A, the first three data points show the initial concentration of 1-butene as being between about 4400 ppm and 4450 ppm prior to feeding H$_2$ into the system. As the hydrogenation reaction proceeds, the feed concentration of 1-butene increases, suggesting that 1,3-butadiene and vinylacetylene are converting to 1-butene. Moreover, FIG. 2B also illustrates that as the reaction proceeds, a sharp increase in 2-butenes concentration is observed to a steady-state value of about 40 ppm while a sharp decrease in vinylacetylene is seen from about 120 ppm to about 40 ppm. As with FIG. 2A, the first three data points show initial concentrations of 1,3-butadiene, vinylacetylene, 2-butenes, and n-butane. The catalysts maintained its initial activity and selectivity over a period of more than 13 hours without regeneration, indicating a high degree of stability.

Thus, as presented herein, multimetallic platinum-based catalysts are fabricated for the selective hydrogenation of vinylacetylene and 1,3-butadiene to mixtures of butenes where 1-butene is a main product and minimal formation of the exhaustively hydrogenated product, n-butane, and isomerized species (e.g., 2-butenes) is observed. Catalysts used in the synthesis procedure have improved stability, high selectivity to monoolefins, and increased atomic efficiency of the catalytic metal. Superior hydrogenation activity and selectivity is achieved using monodispersed Pt sites or small clusters compared to nanoparticles. Promoters (specifically, for example, boron) significantly favor hydrogenation of vinylacetylene and 1,3-butadiene to the mono-olefin (1-butene) and suppress the deposition of coke under harsh dehydrogenation conditions (200° C. or higher). Hydrogenation selectivity to butenes of at least 90% may be achieved. Additionally, the catalysts disclosed herein may also be recyclable.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

References herein to the positions of elements (i.e. "top," "bottom," "above," "below," "on," etc.) are merely used to describe the orientation of various elements in the FIGURES. It should be noted that the orientation of various elements may differ according to other exemplary embodiments, and that such variations are intended to be encompassed by the present disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed:

1. A method of forming a mixture of 1-butene and 2-butenes comprising:
    exposing a C4 feedstock contaminant to a catalyst comprising $M'/M/E_xO_y$, where the catalyst metal M' is a Pt metal, the promotor M is a material selected from the group consisting of B, Zn, and Sn wherein the promotor has a structure selected from the group consisting of monolayer, single metal sites, or extended structures and $E_xO_y$ is a substrate where E is Si, Al, Ti, or Zr and x and y represent stoichiometric amounts; and
    forming the mixture of 1-butene and 2-butenes.

2. The method of claim 1, wherein forming the mixture comprises a selectivity for 1-butene and 2-butene of at least 80%.

3. The method of claim 1, wherein exposing the C4 feedstock contaminant is at a temperature of approximately 200° C.

4. The method of claim 1, wherein at least 70% of the C4 feedstock contaminant is converted to the mixture.

5. The method of claim 1, wherein the C4 feedstock contaminant is 1,3-butadiene, vinylacetylene, or a combination thereof.

6. The method of claim 1, wherein the catalyst comprises the catalyst deposited on the promotor M which is deposited on the substrate and further wherein exposing the C4 feedstock comprises exposing the C4 feedstock to the catalyst metal.

7. The method of claim 1, wherein the catalyst comprises promotor deposited on the catalyst which is deposited on the substrate and further wherein exposing the C4 feedstock comprises exposing the C4 feedstock to the promotor.

* * * * *